United States Patent
Worku et al.

(10) Patent No.: US 9,752,010 B2
(45) Date of Patent: Sep. 5, 2017

(54) PHOSPHORUS-CONTAINING COMPOUNDS USEFUL FOR MAKING HALOGEN-FREE, IGNITION-RESISTANT POLYMERS

(71) Applicant: Blue Cube IP LLC, Midland, MI (US)

(72) Inventors: Anteneh Z. Worku, Pearland, TX (US); Michael J. Mullins, Houston, TX (US)

(73) Assignee: BLUE CUBE IP LLC, Midland, MI (US)

( * ) Notice: Subject to any disclaimer, the term of this patent is extended or adjusted under 35 U.S.C. 154(b) by 0 days.

(21) Appl. No.: 15/207,225

(22) Filed: Jul. 11, 2016

(65) Prior Publication Data

US 2016/0319107 A1 Nov. 3, 2016

Related U.S. Application Data

(62) Division of application No. 14/110,939, filed as application No. PCT/US2012/035933 on May 1, 2012, now Pat. No. 9,388,297.

(60) Provisional application No. 61/489,705, filed on May 25, 2011.

(51) Int. Cl.

| | | |
|---|---|---|
| *C08K 5/51* | (2006.01) | |
| *C07F 9/6571* | (2006.01) | |
| *C08K 5/527* | (2006.01) | |
| *C08K 5/5393* | (2006.01) | |
| *C08K 5/5313* | (2006.01) | |
| *C09J 11/06* | (2006.01) | |
| *C07F 9/28* | (2006.01) | |
| *C08J 5/24* | (2006.01) | |
| *C09D 163/04* | (2006.01) | |
| *C09J 163/04* | (2006.01) | |
| *H05K 1/03* | (2006.01) | |
| *C08K 5/00* | (2006.01) | |

(52) U.S. Cl.
CPC .................. *C08K 5/51* (2013.01); *C07F 9/28* (2013.01); *C07F 9/657172* (2013.01); *C07F 9/657181* (2013.01); *C08J 5/24* (2013.01); *C08K 5/527* (2013.01); *C08K 5/5313* (2013.01); *C08K 5/5393* (2013.01); *C09D 163/04* (2013.01); *C09J 11/06* (2013.01); *C09J 163/04* (2013.01); *H05K 1/0353* (2013.01); *C08J 2363/04* (2013.01); *C08K 5/0066* (2013.01)

(58) Field of Classification Search
CPC ................................ C08K 5/0066; C08K 5/51
See application file for complete search history.

(56) References Cited

U.S. PATENT DOCUMENTS

| | | |
|---|---|---|
| 1,223,033 A | 4/1917 | Cole |
| 4,621,123 A | 11/1986 | Takagishi |
| 5,157,080 A | 10/1992 | Gardner |
| 5,698,729 A | 12/1997 | Kleiner |
| 2007/0221890 A1 | 9/2007 | Gan |
| 2008/0102391 A1 | 5/2008 | Yanagawa |

FOREIGN PATENT DOCUMENTS

| | | |
|---|---|---|
| GB | 1439092 | 6/1976 |
| WO | 2005118604 | 12/2005 |

OTHER PUBLICATIONS

Aliouane N et al: "Sythesis of New Benzylic Di-, Tri, and Tetraphosphonic Acids as Potential Chelating Agents", Sulfur and Silicon and the Related Elements, vol. 186, No. 2, 2011, pp. 354-364.
Arbusow; Pure Appl. Chem. 9: 307-353.
Boehmer V et al: "(o-Hydroxyphenyl)nriethylphosphinc acids: Synthesis and potentiometric determinations of their Values", Helvetica Chimica Acta, vol. 76, No. 1, Feb. 10, 1993, pp. 139-149.
Bondarenko N A et al: "Synthesis of a-substituted phosphinyl-,; phosphinylmethyl-and phosphinylethylphenols", Bulletin of the Academy of Sciences of the USSR; Division of Chemical Sciences, vol. 28, No. 2, Feb. 1979, pp. 399-403.
Chasar D W: "Reexamination of the Reaction of Triethyl Phosphite with o-Hydroxybenzyl Alcohol", Journal of Chemistry, vol. 48, No. 24, Dec. 1983, pp. 4768-4769.
Harrison A et al: "Synthesis, structure and magnetic properties of [Cu4(Huribpp)2(H2NC(0)NH2)2(H20)8].4H20", Transactions, No. 22, 2003, pp. 4271-4274.
Ivanov B E et al: "Mechanism of the interaction of o-hydroxybenzyl alcohol with trialkyl phosphites", Bulletin of the Academy of Sciences of the USSR; Division of Chemical Sciences, vol. 18, No. 9, Sep. 1969, pp. 1770-1774.
Kaiser J et al: "Cation exchange resins based on phosphonomethyl-substituted phenols", Makromolefulare Chemie, vol. 193, No. 3, Mar. 1992, pp. 799-810.
Keglevich et al, Transition Metal Chemistry, Platinum (II) complexes of 2-alkoxy-dibenzo[c.e]-[1,2] oxaphosphorines, 33; 505-510 (2008).
Perez-Prieto J et al: "Influence of Substitution at the Benzylic Position on the Behavior of Sterioisomeric Phosphorus Compounds as Precursors of Stabilized Carbon-Centered Radicals", Organic Letters, vol. 7, No. 18, Sep. 2005, pp. 3869-3872.

(Continued)

Primary Examiner — Megan McCulley
(74) Attorney, Agent, or Firm — Polsinelli PC

(57) ABSTRACT

A process for making a phosphorus-containing compound is disclosed. The process comprises contacting a compound of formula (A) wherein $R^A$ and $R^B$ are selected from optionally substituted aryl, aryloxy, alkyl and alkoxy groups or can be combined to form cyclic structures; and $R^C$ is methyl, ethyl, isopropyl, n-butyl, i-butyl, t-butyl, phenyl or benzyl; and a compound of formula (B) wherein $R^1$-$R^4$ are selected from optionally substituted aryl, aryloxy, alkyl and alkoxy groups. The phosphorus-containing compound can then be used as a flame retardants for polymers, especially for epoxy, polyurethane, thermosetting resins and thermoplastic polymers. Such flame retardant-containing polymers can be used to make protective coating formulations and ignition-resistant fabricated articles, such as electrical laminates, polyurethane foams, and various molded and/or foamed thermoplastic products.

14 Claims, No Drawings

(56) References Cited

OTHER PUBLICATIONS

Vogt W: "Reaction of o-hydroxybenzyl alcohols with esters of acids of phosphorus with a coordination No. 3", Phosphorus and Sulfur and the Related Elements, vol. 5, No. 1, 1978, pp. 123-125.
PCT/US2012/035933, International Search Report & Written Opinion of the International Searching Authority dated Nov. 27, 2012.
PCT/US2012/035933, International Preliminary Report on Patentability dated Dec. 5, 2013.
Bhattacharya; Chem. Rev., The Michaelis-Arbuzov Rearrangement, 81: 415-430.
U.S. Appl. No. 14/110,939 Restriction Requirement dated Aug. 24, 2015.
U.S. Appl. No. 14/110,939 Response to Restriction Requirement dated Sep. 24, 2015.
U.S. Appl. No. 14/110,939 Non-Final Rejection dated Dec. 17, 2015.
U.S. Appl. No. 14/110,939 Response to Non-Final-Office Action dated Feb. 4, 2016.

PHOSPHORUS-CONTAINING COMPOUNDS USEFUL FOR MAKING HALOGEN-FREE, IGNITION-RESISTANT POLYMERS

This application is a non-provisional application claiming priority from the U.S. Provisional Patent Application No. 61/489,705, filed on May 25, 2011, entitled "PHOSPHORUS-CONTAINING COMPOUNDS USEFUL FOR MAKING HALOGEN-FREE, IGNITION-RESISTANT POLYMERS" the teachings of which are incorporated by reference herein, as if reproduced in full hereinbelow.

The present invention is in the field of phosphorus-containing compounds; their use as flame retardants for polymers, especially for epoxy, polyurethane, thermosetting resins and thermoplastic polymers; and the use of such flame retardant-containing polymers to make protective coating formulations and ignition-resistant fabricated articles, such as electrical laminates, polyurethane foams, and various molded and/or foamed thermoplastic products.

Ignition-resistant polymers have typically utilized halogen-containing compounds to provide ignition resistance. However, there has been an increasing demand for halogen-free compositions in ignition-resistant polymers markets. Phosphorus-based flame retardants that are reactive with epoxy resins are being commercialized for use in thermoset epoxy resin formulations. However, such flame resistance must be prepared using a multi-step processes, and are therefore relatively expensive to produce. Also, processes described in the prior art give mixtures of oligomers that are difficult to characterize.

Therefore, there remains a need to provide a reactive halogen-free flame retardant that can be prepared less expensively compared to those materials described in the prior art and can be produced with high purity.

SUMMARY OF THE INVENTION

A process for making a phosphorus-containing compound comprising, consisting of, or consisting essentially of contacting:

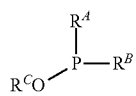

(A)

wherein $R^A$ and $R^B$, independently of one another, are selected from the group consisting of substituted aryl groups, substituted aryloxy groups, unsubstituted aryl groups, unsubstituted aryloxy groups, substituted alkyl groups, substituted alkoxy groups, unsubstituted alkyl groups, and unsubstituted alkoxy groups;

or wherein $R^A$ and $R^B$ are be combined to form cyclic structures;

wherein $R^C$ is a hydrocarbyl radical containing in the range of from 1 to 12 carbon atoms per molecule and is selected from the group consisting of methyl, ethyl, isopropyl, n-butyl, i-butyl, t-butyl, phenyl, and benzyl; and

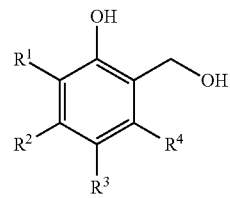

(B)

wherein $R^1$-$R^4$, independently from one another, are selected from the group consisting of hydrogen, a substituted alkyl group, a substituted alkoxy group, an unsubstituted alkyl group, an unsubstituted alkoxy group, a substituted aryl group, a substituted aryloxy group, an unsubstituted aryl group and an unsubstituted aryloxy group.

Definitions

The terms "organo" and "organic" as used herein refer to compounds or moieties comprising carbon atoms and hydrogen atoms, and optionally hetero atoms (that is, atoms which are not carbon or hydrogen), which are primarily covalently bonded to one another. Preferred optional hetero atoms include oxygen atoms and nitrogen atoms. The number of hetero atoms in the "organo" and "organic" compounds and moieties is less than the number of carbon atoms, and is preferably less than half the number of carbon atoms.

The terms "hydrocarbyl" and "hydrocarbylene" refer to chemical structures or moieties comprising carbon atoms and hydrogen atoms covalently bonded to each other. Such structures or moieties may contain atoms other than, and in addition to, carbon and hydrogen (referred to herein as "hetero" atoms) insofar that the hetero atoms do not add significant reactive functionality to such moieties. Examples of such acceptable hetero atoms are ether oxygen or thioether sulfur atoms. Such moieties preferably do not contain any hetero atoms.

The expression "wt. percent" means "weight-percent".
The expression "-OMe" stands for a methoxy group.

Phosphorus-Containing Product

The phosphorus-containing product of the present invention, is obtainable from the reaction between Component (A), and Component (B). The product of the present invention contains a phosphorus element in its chemical structure making it useful as a raw material for preparing flame resistant materials. In this embodiment, the product can be considered as a crosslinking agent, curing agent or hardener for an epoxy resin.

The product of the present invention generally has a phosphorus content of at least 4 weight-percent and, in another embodiment, at least 6 weight-percent, making it useful as a flame retardant material. The product is preferably substantially free of bromine atoms, and more preferably substantially free of halogen atoms.

Organophosphorus-Containing Compounds, Component (A)

The organophosphorus-containing compound, Component (A), is generally represented by a formula with the structure of Formula (I), below.

Formula (I)

The phosphorus atom may be bonded to two separate organic moieties or may be bonded to one organic moiety. When bonded to one organic moiety, the bonds may connect with the same atom of the organic moiety to form a double bond or, preferably, may be single bonds connecting the phosphorus atom with different atoms in the same organic moiety.

"$R^A$" and "$R^B$" may be the same or different and are selected from substituted or unsubstituted aryl or aryloxy groups, substituted or unsubstituted alkyl or alkoxy group and "$R^C$" being a hydrocarbyl radical with 1 through 12 carbons such as methyl, ethyl, isopropyl, n-butyl, i-butyl, t-butyl, phenyl, or benzyl. "$R^A$" and "$R^B$" can be combined to give cyclic structures such as neopentyl glycol, ethylene glycol or catechol based structures.

In an embodiment, the organophosphorus-containing compound, Component (A), corresponds to one of the following chemical Formulae (III) to (V):

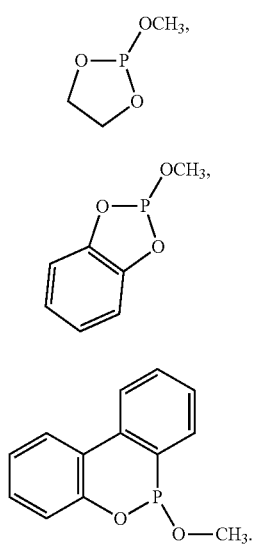

Formula (III)

Formula (IV)

Formula (V)

Formula (V) is 9,10-dihydro-9-oxa-10-phosphaphenan-threne-10-oxide-methoxy (also known as "DOP-OMe").

The organophosphorus-containing compound, Component (A), is preferably substantially free of bromine atoms, more preferably substantially free of halogen atoms.

Synthesis of Component (A)

Component (A) can be synthesized by any suitable method. Organo-phosphites, phosphonites and phosphinites (trivalent phosphorus compounds with 3, 2, or 1 oxygen-phosphorus bonds, respectively) can be obtained by reacting the corresponding phosphorus trihalide, alkyl phosphorus dihalide, and dialkyl phosphorus halide with alcohols in presence of bases.

In an embodiment, Component (A) is produced by the following process: the starting material DOP-Cl is obtained by reacting o-phenylphenol with phosphorus trichloride in the presence of zinc chloride catalyst. The experimental procedure is described in US Patent Application Publication No. 20070173659A1.

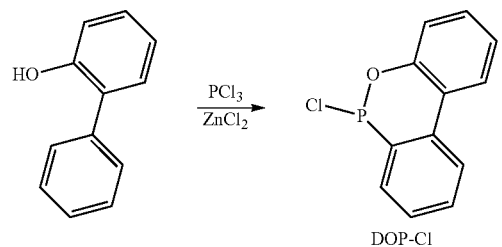

DOP-Cl

As described in US Patent Application Publication No. 20070173659A1, DOP-Cl is known to react with alcohols in the presence of acid acceptors to yield DOP-OMe.

DOP-Cl is reacted with methanol to form DOP-OMe. This is illustrated by the scheme below:

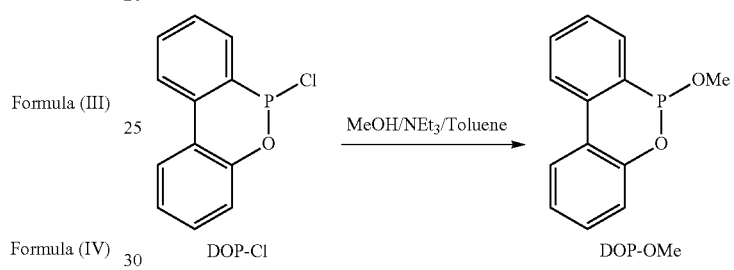

DOP-Cl                    DOP-OMe

In additional embodiments, Component (A) is represented by Formulas (VII)-(IX) below:

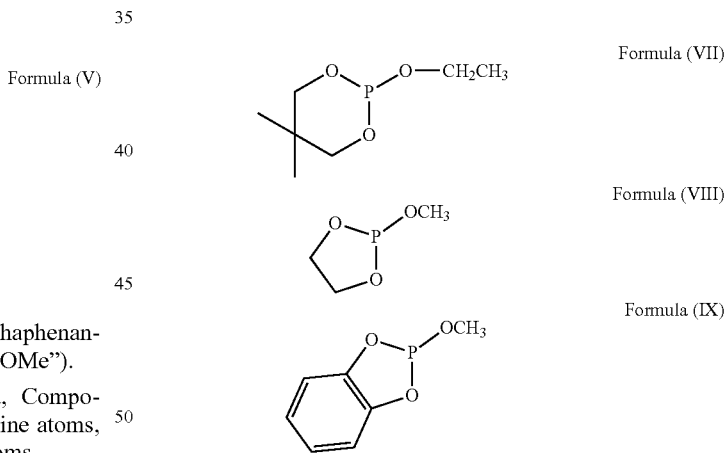

Formula (VII)

Formula (VIII)

Formula (IX)

Compounds Corresponding to Component (B)

Component (B) is generally represented by Formula (X):

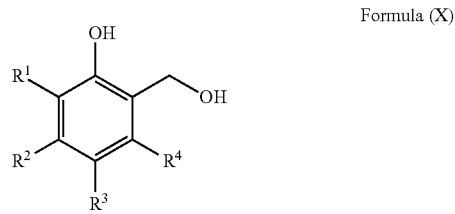

Formula (X)

wherein $R^1$-$R^4$ is hydrogen, a substituted or unsubstituted alkyl or alkoxy group, a substituted or unsubstituted aryl or aryloxy group $R^1$-$R^4$ can be the same or different to form a product.

Component (A) is represented by Formulas (XI)-(XIV) below:

Formula (XI)

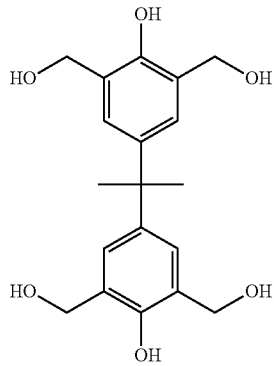

Formula (XII)

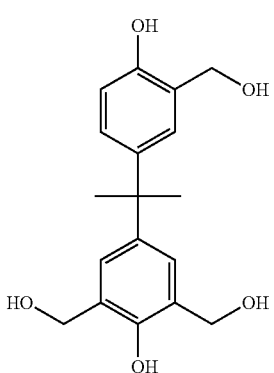

Formula (XIII)

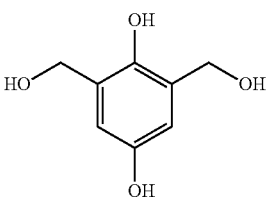

Formula (XIV)

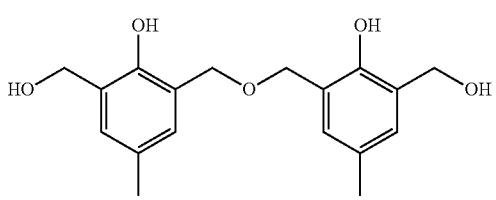

Hydroxymethyl substituted phenols and polyfunctional phenols are known products. Base-catalyzed phenol formaldehyde resins also known as resoles are made by reacting phenols with formaldehyde. Examples are described in U.S. Pat. No. 2,912,395, EP 1 352 888 A1 and US 2003/0022109

A1. Monomeric, oligomeric or polymeric phenol-formaldehyde resins can be synthesized using these methods. An example is shown below for a monomer.

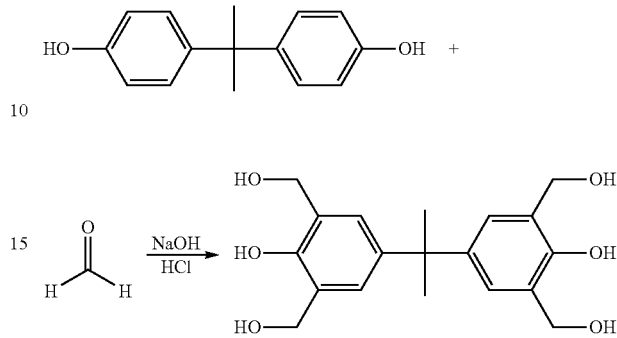

Reaction of Component (A) with Component (B) to Form Compound I

The reaction for making Compound I involves a typical Michaelis-Arbuzov reaction where typically alkyl halides are reacted with phosphites in order to form the corresponding phosphonates, phosphinates and phosphine oxides. (Pure Appl. Chem. 9: 307-353; Chem. Rev. 81: 415-430)

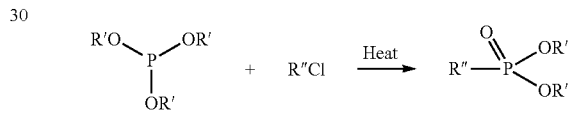

It is not typical for Michaelis-Arbuzov reactions to involve alcohols. In this invention, we have found out that DOP-Cl can be reacted with a benzyl alcohol to undergo an Arbuzov rearrangement to create a P—C bond.

To prepare Compound (I), Component (A) is mixed with Component (B) in a reaction vessel and the mixture is heated at an elevated temperature which is a temperature that is preferably below the decomposition temperature of the starting material. The reaction mixture is heated 60-220° C., preferably up to 100-200° C. and more preferably at 150-200° C.

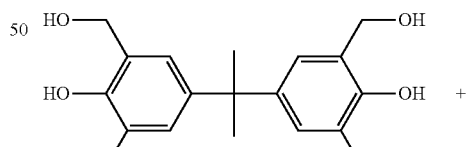

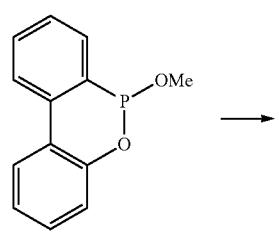

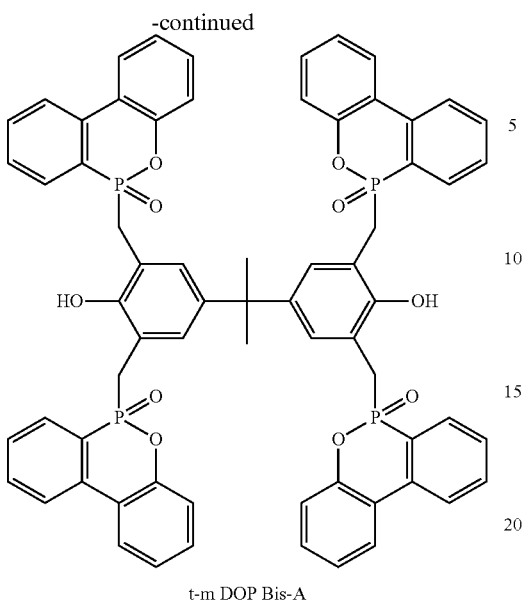

t-m DOP Bis-A

The reaction of the present invention is preferably carried out without the presence of water (generally the water is present in less than 5 wt percent, more preferably less than 3 wt percent and most preferably less than 1 wt percent) because water may tend to react with Component (A). Alcohol is formed as a byproduct of the reaction. The pressure in the reaction vessel can be reduced to a pressure below atmospheric pressure, such as a pressure of 12-300 mm if there is a desire to remove the alcohol. The reaction vessel may optionally be purged with a gas or volatile organic liquid to further assist in removing byproduct(s). The gas or volatile organic liquid is preferably inert to the contents of the reaction vessel.

Component (B) can be used as a solid or can be dissolved in an organic solvent, well known to those skilled in the art, such as xylene, cyclohexanone, Dowanol PMA or Dowanol PM (trademark of The Dow Chemical Company); and part of the solvent can be removed either by heat or applying vacuum to the solution before the addition of Component (A). The order of charging of Component (A) and Component (B) into the reaction mixture is not important.

Components (A) and (B) are preferably combined at a stoichiometric ratio in the range from 1:1 to 4:1, based on total hydroxymethyl functionality of the starting Component B.

The product obtained is of acceptable purity. More purification can be done by dissolving the product in solvents such as chloroform or toluene and precipitating the product by adding diethyl ether. The final product can be dried in a vacuum oven or convection oven where the temperature does not exceed 100° C. The reaction is preferably carried out for a period of time sufficient to a react the P—OR$^C$ moiety of Component (A) with the OH moieties of Component (B). The time of reaction is typically from 30 minutes to 5 hours, preferably from 1 hour to 3 hours, and more preferably from 2 hours to 3 hours.

If desired, other materials such as catalysts or solvents may be added to the reaction mixture of Component (A) and (B).

The phosphorus-containing product of the present invention (Compound I) resulting from the reaction between Component (A) and Component (B) has a phosphorus content of preferably at least about 4 weight-percent, and more preferably at least about 6 weight-percent to make it useful as a flame retardant material. The product is preferably substantially free of bromine atoms, and more preferably substantially free of halogen atoms. Generally, the resulting product from the reaction of Components (A) and (B) may be a blend of one or more of different oligomers.

In additional embodiments, the product can be represented by Formula (XV) below:

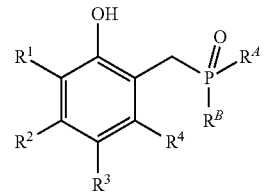

Formula (XV)

wherein $R^1$-$R^4$ is hydrogen, a substituted or unsubstituted alkyl or alkoxy group, a substituted or unsubstituted aryl or aryloxy group. $R^1$-$R^4$ can be the same or different to form a product.

"$R^A$" and "$R^B$" may be the same or different and are selected from substituted or unsubstituted aryl or aryloxy groups, substituted or unsubstituted alkyl or alkoxy group. "$R^A$" and "$R^B$" can be combined to give cyclic structures such as neopentyl glycol, ethylene glycol or catechol based structures. Examples are given in Formulas (XVI) to (XXIII) below:

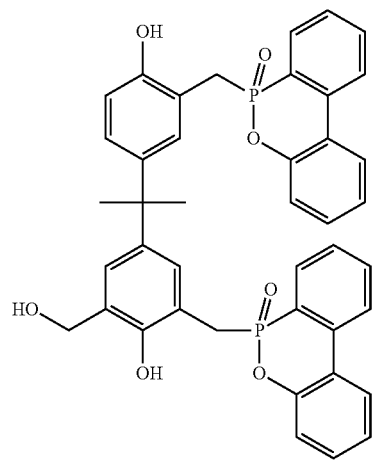

Formula (XVI)

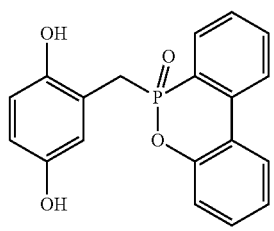

Formula (XVII)

Formula (XVIII)

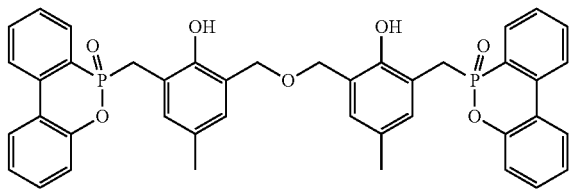

Formula (XIX)

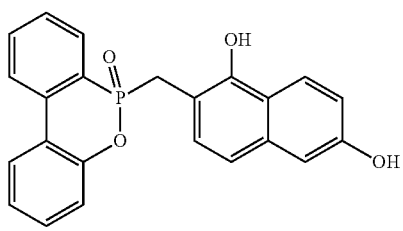

Formula (XX)

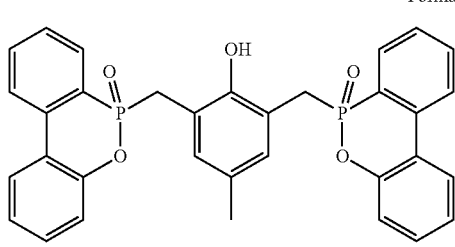

Formula (XXI)

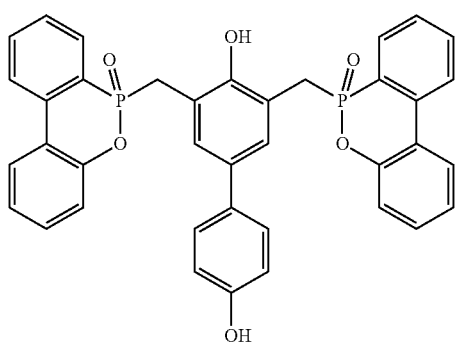

Formula (XXII)

Formula (XXIII)

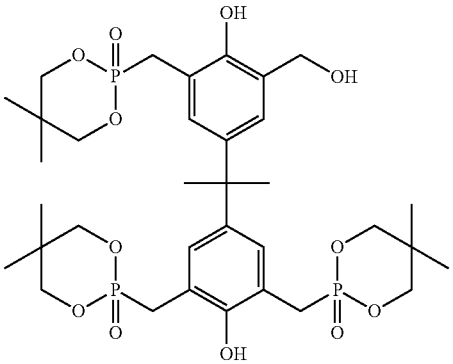

Epoxy Resin Compositions

Applications of Compound (I) are described in WO 2005/118604 A1.

In one embodiment of the present invention, the phosphorus-containing product obtainable by reacting Component (A) with Component (B), as described above, may be used, as one component, of a curable (crosslinkable) phosphorus-containing flame resistant epoxy resin composition.

In another embodiment, the product may be first reacted with an epoxy compound to form a phosphorus-containing epoxy compound (herein referred to as an "epoxidized compound"), and then subsequently the epoxidized compound may be combined with at least one curing agent to form the curable flame-retardant epoxy resin composition as described in WO 2005/118604 A1.

The compositions of the present invention can be used to make composite materials by techniques well-known in the industry, such as by pultrusion, molding, encapsulation, or coating. The present invention is particularly useful for making adhesive, coatings, composites, castings, potting materials, B-staged prepregs, laminates, bonding sheets, and resin coated copper foils by well known techniques in the industry.

EXAMPLES

The following examples are intended to be illustrative of the present invention and to teach one of ordinary skill in the art to make and use the invention. These examples are not intended to limit the invention in any way.

Synthesis of DOP-OMe

In a 1 liter reactor, 23.5 grams (0.1 mol) of DOP-Cl and 10.1 grams (0.1 mol) of triethylamine was added to 100 mL of stirring toluene under nitrogen. The mixture was cooled using an ice/salt bath. A 3.2 gram quantity (0.1 mol) of methanol was added slowly via addition funnel keeping the reaction temperature at 0-10° C. After the addition of methanol was completed, the cooling bath was replaced with a heating mantle and the reaction mixture was heated to 50° C. and stirred continuously for an additional 3 hours. The heating mantle was then removed and the reaction mixture was allowed to cool to room temperature. The triethylamine hydrochloride salt was filtered off and the filtrate was concentrated using the rotary evaporator under full vacuum keeping the bath temperature below 100° C. Crude yield of DOP-OMe: 90%, light yellow oil. The product could be used for the next step without further purification.

Synthesis of tetramethylol Bis-A

A 110.5 gram quantity (0.48 mol) of DOP-OMe and 34.7 grams (0.1 mol) of tetramethylol Bis-A were weighed out into a 500 mL one neck RB flask. The mixture was then attached to a Kugelrohr set-up with one receiving flask. The flasks were secured by applying 200 mm vacuum using a vacuum pump. The heating chamber was heated to 100° C. and was kept at that temperature for 30 minutes upon which methanol started condensing in the receiving flask. The reaction mixture was then heated slowly to 170° C. over 30 minutes and was kept at that temperature for another 30 minutes. The heating was then stopped and the formed solid was allowed to cool to room temperature. The reaction flask was then removed and 200 mL of chloroform was added to dissolve the solid product. The solution was transferred to an Erlenmeyer flask. While stirring, 100 mL of diethylether was added. The precipitated white solid was suction filtered using vacuum and was dried in a vacuum oven at 50° C. Crude yield: 101 grams of t-mDOP Bis-A Evaluation of t-mDOP Bis A in an Epoxy Formulation Control Formulation:

A comparison was made using a halogen free phosphorus functionalized control formulation containing XZ-92741, a commercial hardener available from The Dow Chemical Company. The components used in the formulation are given in the table below.

| Designation | Description |
|---|---|
| DEN ™ 438 | Liquid epoxy novolac resin having an epoxide equivalent weight Liquid epoxy novolac resin, available from The Dow Chemical Company |
| XZ-92741 | Phosphorus containing epoxy hardener available from The Dow Chemical Company |
| DICY | Dicyandiamide |
| MEK | Methyl ethyl ketone (an organic solvent) |
| 2-PI | 2-Phenyl imidazole |

The comparison was done by replacing XZ-92741 with t-mDOP Bis-A. Preparation of the varnish was accomplished following the procedure below.
1. Prepare 10 wt. % DICY solution using dimethylformamide as a solvent
2. Prepare 20 wt. % solution of 2-phenylimidazole (2-PI) using DOWANOL™ PM as a solvent
3. Add the DICY and 2-PI solution (2-PI) to XZ 92741.00 Hardener and stir until a homogeneous solution is obtained.
4. Add DEN™ 438 Epoxy Resin Solution Stroke cure reactivity is determined using IPC-TM-650 No. 2.3.17. A timer was started as soon as 1.5 ml of the varnish was placed on a hotplate at 171° C. The varnish was left to sit on the hot plate for one minute prior to being manipulated with a wooden tongue depressor in order to evaporate residual solvent. The varnish was manipulated and mixed and determined to be gelled when the material could not form strings when lifted from the surface of the hot plate. The total time was recorded as the stroke cure reactivity or gel time.

The gelled resin was then collected and placed in an oven at 190-200° C. to post cure for 1.5 h. Small pieces of the post cured resin were placed in a thermal gravimetric analyzer (TGA Q50 or 2050, TA Instruments) to obtain a decomposition temperature, $T_d$, which is defined as the temperature at which 5% weight loss of the sample occurs. The TGA measurements were done at a heating rate of 10°/min under nitrogen atmosphere. The resin was also analyzed using differential scanning calorimeter (DSC Q1000, TA Instruments) to measure the glass transition temperature, $T_g$ of the formulation. The method used was IPC TM-650 2.4.25.

| | DSC Method |
|---|---|
| 1 | Equilibrate at 40° C. |
| 2 | Ramp 10.00° C./min to 220° C. |
| 3 | Equilibrate at 200° C. |
| 4 | Isothermal for 15 min |
| 5 | Equilibrate at 40° C. |
| 6 | Ramp 10.00° C./min to 220° C. |
| 7 | Equilibrate at 40° C. |
| 8 | Ramp 20.00° C./min to 220° C. |

Comparison was done between a formulation containing XZ-92741, a proprietary phosphorus containing Epoxy resin and a formulation where XZ-92741 is replaced by t-mDOP Bis-A. The formulation was done at the same wt. % P loading. The glass transition temperature (Tg) was measured by DSC using a TA Instruments Model Q2000 DSC.

The inventive example formulation is shown in Table I below.

TABLE I

| Material | Control Solids % | Inventive Example Solids % |
|---|---|---|
| D.E.N. ™438 [85% solids in MEK] | 63.00 | 68.79 |
| XZ-92741 (59% solids in MEK) | 37.00 | |
| t-mDOP Bis-A | | 30.56 |
| Dicy (10 wt % in DMF) | 2.40 | 3.05 |
| 2-PI (20 wt. % in Dowanol PM | 1.60 | 1.60 |
| % P | 3.20 | 3.20 |
| Epoxy:hardner ratio | 1.24 | 1.24 |

The $T_g$ values for the control and inventive examples are shown in Table II, below.

TABLE II

| | Reactivity (s) | $T_g1$ (° C.) | $T_g2$ (° C.) | $T_g3$ (° C.) | $T_d$ (° C.) |
|---|---|---|---|---|---|
| Control | 164 | 167 | 168 | 169 | 349 |
| t-mDOP Bis-A | 205 | 172 | 175 | 178 | 354 |

The data shows that t-mDOP Bis-A formulation shows improved Tg.

What is claimed:

1. A process for making a curable phosphorus-containing epoxy resin composition comprising blending:
   (I) a phosphorus-containing compound comprising the reaction product of:

(A)

wherein $R^A$ and $R^B$, independently of one another, are selected from the group consisting of substituted aryl groups, substituted aryloxy groups, unsubstituted aryl groups, unsubstituted aryloxy groups, substituted alkyl groups, and unsubstituted alkyl groups;

or wherein $R^A$ and $R^B$ are be combined to form cyclic structures;

wherein $R^c$ is a hydrocarbyl radical containing in the range of from 1 to 12 carbon atoms per molecule and is selected from the group consisting of methyl, ethyl, isopropyl, n-butyl, i-butyl, t-butyl, phenyl, and benzyl; and

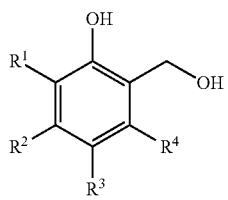
(B)

wherein $R^1$-$R^4$, independently from one another, are selected from the group consisting of hydrogen, a substituted alkyl group, a substituted alkoxy group, an unsubstituted alkyl group, an unsubstituted alkoxy group, a substituted aryl group, a substituted aryloxy group, an unsubstituted aryl group and an unsubstituted aryloxy group;

(II) at least one epoxy resin; and (III) at least one catalyst.

2. A phosphorus-containing compound prepared by a process comprising contacting:

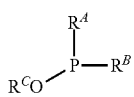
(A)

wherein $R^A$ and $R^B$, independently of one another, are selected from the group consisting of substituted aryl groups, substituted aryloxy groups, unsubstituted aryl groups, unsubstituted aryloxy groups, substituted alkyl groups, and unsubstituted alkyl groups;

or wherein $R^A$ and $R^B$ are be combined to form cyclic structures;

wherein $R^C$ is a hydrocarbyl radical containing in the range of from 1 to 12 carbon atoms per molecule and is selected from the group consisting of methyl, ethyl, isopropyl, n-butyl, i-butyl, t-butyl, phenyl, and benzyl; and

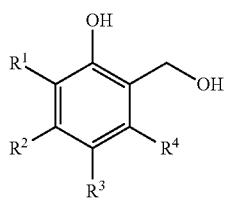
(B)

wherein $R^1$-$R^4$, independently from one another, are selected from the group consisting of hydrogen, a substituted alkyl group, a substituted alkoxy group, an unsubstituted alkyl group, an unsubstituted alkoxy group, a substituted aryl group, a substituted aryloxy group, an unsubstituted aryl group and an unsubstituted aryloxy group.

3. A phosphorus-containing compound prepared by a process comprising contacting:

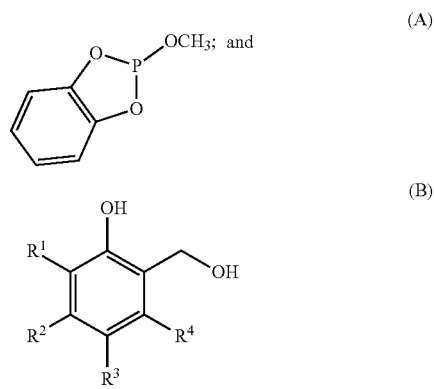

wherein $R^1$-$R^4$, independently from one another, are selected from the group consisting of hydrogen, a substituted alkyl group, a substituted alkoxy group, an unsubstituted alkyl group, an unsubstituted alkoxy group, a substituted aryl group, a substituted aryloxy group, an unsubstituted aryl group and an unsubstituted aryloxy group.

4. A varnish produced from the composition of claim 1.

5. A prepreg prepared from the varnish of claim 4.

6. An electrical laminate prepared from the varnish of claim 4.

7. A printed circuit board prepared from the varnish of claim 4.

8. A coating prepared from the composition of claim 1.

9. A composite prepared from the composition of claim 1.

10. A casting prepared from the composition of claim 1.

11. An adhesive prepared from the composition of claim 1.

12. The process of claim 1, wherein compound (B) is defined by the following formula:

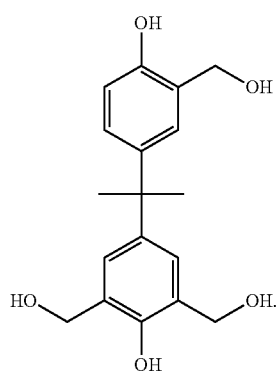 [SMILES: CC(C)(c1ccc(O)c(CO)c1)c1cc(CO)c(O)c(CO)c1]

13. The process of claim 1, wherein compound (B) is defined by the following formula:

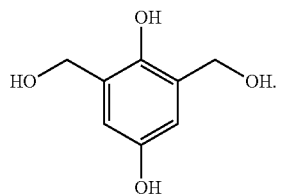 [SMILES: OCc1cc(O)cc(CO)c1O]
14. The process of claim 1, wherein compound (B) is defined by the following formula:
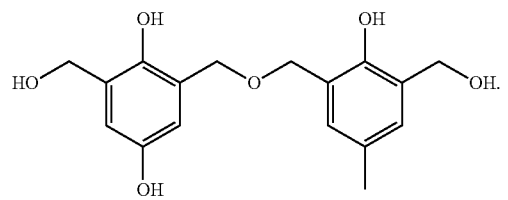 [SMILES: Cc1cc(CO)c(O)c(COCc2cc(O)cc(CO)c2O)c1]
* * * * *